United States Patent [19]

Mason et al.

[11] Patent Number: 4,689,169

[45] Date of Patent: Aug. 25, 1987

[54] DRY COMPOSITIONS FOR THE PRODUCTION OF CHLORINE DIOXIDE

[75] Inventors: John Y. Mason, Plymouth; Bruce W. Hicks, Rio Linda, both of Calif.

[73] Assignee: Rio Linda Chemical Company, Inc., Sacramento, Calif.

[21] Appl. No.: 743,749

[22] Filed: Jun. 12, 1985

Related U.S. Application Data

[62] Division of Ser. No. 550,560, Nov. 10, 1983, Pat. No. 4,547,381.

[51] Int. Cl.$^4$ ................................................ C09K 3/00
[52] U.S. Cl. ........................... 252/186.24; 252/187.23; 426/316
[58] Field of Search .................. 422/29; 426/316, 318; 252/186.2, 186.24, 187.23

[56] References Cited

U.S. PATENT DOCUMENTS

| | | | |
|---|---|---|---|
| 2,482,891 | 9/1949 | Aston | 252/187.23 |
| 3,591,515 | 7/1971 | Lovely | 252/186.22 |
| 3,967,039 | 6/1976 | Ninane et al. | 252/187.23 X |
| 3,997,462 | 12/1976 | Denaeyer et al. | 252/187.23 |
| 4,104,190 | 8/1978 | Hartshorn | 252/187.21 |
| 4,547,381 | 10/1985 | Mason et al. | 252/187.23 |
| 4,585,482 | 4/1986 | Tice et al. | 252/187.23 X |

*Primary Examiner*—Matthew A. Thexton
*Attorney, Agent, or Firm*—Leonard Bloom

[57] ABSTRACT

A dry composition for the sustained, controlled production of gaseous chlorine dioxide comprising a dry, inert diluent; a metal chlorite selected from the group consisting of alkali metal chlorites and alkaline earth metal chlorites; and a dry agent capable of reacting with a metal chlorite in the dry state to produce chlorine dioxide, said agent being selected from the group consisting of dry oxidizing agents and dry acids. The composition of the invention is manufactured using solely dry constituents, thereby obviating an intensive drying step and resulting in substantial savings as well as simplifying the manufacturing process. The compositions of the invention find particular utility in applications involving the controlled generation of chlorine dioxide for a sustained period of time for the preservation of boxed fruits and vegetables during transportation or in deodorizing enclosed spaces such as refrigerators or lockers.

13 Claims, No Drawings

DRY COMPOSITIONS FOR THE PRODUCTION OF CHLORINE DIOXIDE

This application is a division of application Ser No. 550,560, filed Nov. 10, 1983, now U.S. Pat. No. 4,547,381.

BACKGROUND OF THE INVENTION

Chlorine dioxide is known to be an excellent disinfectant as well as a strong oxidizing agent. Its bactericidal, viricidal, algicidal, fungicidal, bleaching, and deodorizing properties are well documented in the prior art. Also known to the prior art is the difficulty of storing and transporting chlorine dioxide, resulting in various apparatuses and compositions to accomplish the on-site production of chlorine dioxide.

Generators for the on-site production of chlorine dioxide in large scale applications such as treating drinking water or industrial process water are well known. An example of such a generator is disclosed in U.S. Pat. No. 4,247,531. However, such generators do no lend themselves to small scale, long term controlled release of chlorine dioxide such as is necessary in the preservation of boxed citrus fruit during shipping or in deodorizing enclosed spaces such as refrigerators or lockers.

For small scale applications, stabilized chlorine dioxide solutions or metal chlorite solutions that liberate chlorine dioxide when acidified, are known in the art. One method of producing a stabilized chlorine dioxide solution is disclosed in U.S. Pat. No. 3,123,521. Other, slightly different methods of producing these solutions are disclosed in U.S. Pat. No. 3,278,446 and U.S. Pat. No. 3,271,242. In certain small scale applications, such as the protection of polant or animal products from bacterial and fungal attack during the shipping and storage of such products, these liquid products are disadvantageous because of the difficulty in packaging and application as well as the danger of contamination of the food products due to spillage. Another disadvantage of such solutions is the fact that they must be acidified in order to release chlorine dioxide. Yet another disadvantage is the difficulty in controlling the rate of release of chlorine dioxide which often results in unacceptably high concentrations of the chlorine dioxide gas.

Powdered or dry compositions that release chlorine dioxide upon addition of water might be considered able to solve the foregoing problems associated with stabilized chlorine dioxide or metal chlorite solutions. Such dry compositions are disclosed in U.S. Pat. Nos. 2,071,091; 2,071,094; 2,022,262; and 2,482,891. However, these prior art dry compositions do not provide for a dry diluent to control release rates and they are accordingly prone to uncontrolled overproduction of chlorine dioxide. In addition, these prior art compositions must be mixed with water or water vapor in order to generate chlorine dioxide. The water addition step effectively imparts to these dry compsotitions the same limitations and disadvantages of the liquid solutions mentioned above.

A method of adsorbing sodium chlorite solutions or chlorine dioxide solutions onto a dry, powdered adsorbant that releases chlorine dioxide in the presence of a powdered, hydrated acid at a pH of less than about 6 is disclosed in U.s. Pat. No. 3,591.515 and the Japanese counterpart, Japanese Pat. No. 48-32079. However, this method of producing a dry chlorine dioxide release composition and the resultant chlorine dioxide release compositions have many drawbacks. Although the foregoing are disclosed as substantially dry compositions, it is obvious that an energy intensive drying step must be involved since the chlorite solutions utilized are only 6% in concentration, close to 90% of the solution beng water. Another drawback of these compositions is that the amount of chlorite or latent chlorine dioxide available is limited to the amount the pulverent adsorbant is capable of adsorbing so that the amount of chlorine dioxide available is limited. Another drawback of such compositions is that, since the chlorine dioxide or sodium chlorite solutions are adsorbed onto the dry adsorbant uniformly, all the adsorbant material has chlorite on it. Accordingly, when such materials are mixed with a powdered, hydrated acid material, all of the acid material will be in contact with adsorbant containing chlorite, thereby resulting in an uncontrolled release of chlorine dioxide.

SUMMARY OF THE INVENTION

This invention provides a dry composition capable of the sustained, controlled production of gaseous chlorine dioxide. The compositions of the invention find utility in the disinfection and deodorizing of enclosed spaces and in the preservation of boxed fruits and vegetables during shipment. Broadly stated, the dry compositions of the invention comprise a metal chlorite; a dry, inert diluent; and a dry agent capable of reacting with said metal chlorite in the dry state to produce chlorine dioxide.

It is therefore an object of this invention to provide for a dry, powdered or granular chlorine dioxide-releasing composition which is manufactured utilizing a completely dry process.

It is another object of this invention to provide a dry, powdered or granular composition which releases chlorine dioxide without the need for water or water vapor activation.

It is still another object of this invention to provide a dry, powdered or granular composition for the release of chlorine dioxide that utilizes a dry diluent to impart a physical space between the reactants, i.e., a dry metal chlorite and a dry agent capable of reacting with said chlorite in the dry state to thereby accomplish the sustained and controlled release of chlorine dioxide.

Yet another object of this invention is to provide a dry chlorine dioxide-releasing composition that is flexible in the ratio of dry metal chlorite, dry diluent, and dry agent capable of reacting with said metal chlorite to release chlorine dioxide, resulting in a wide range of chlorine dioxide release rates.

It is still another object of this invention to provide a dry composition for the generation of chlorine dioxide that, upon agitation, is capable of renewed chlorine dioxide generation.

Other objects and advantages of the present invention will be apparent from the following detailed description.

The foregoing and other objects are accomplished by the practice of this invention.

Broadly, viewed in one of its principal aspects, this invention consists of a dry composition for the sustained, controlled production of gaseous chlorine dioxide comprising:

1. A dry, inert diluent;

2. A metal chlorite selected from the group consisting of alkali metal chlorites and alkaline earth metal chlorites, and 3. A dry agent capable of reacting with said metal chlorite in the dry state to produce chlorine dioxide, said agent being selected from the group consisting of dry oxidizing agents, dry acids, and combinations thereof.

The foregoing compositions find utility in the disinfection and deodorizong of enclosed spaces and in the preservation of boxed fruits and vegetables during shipment. The invention provides for a method of disinfecting and deodorizing an enclosed space consisting of placing in said enclosed space a dry composition for the sustained, controlled release of chlorine dioxide, said composition comprising a dry, inert diluent; a metal chlorite selected from the group consisting of alkali metal chlorites and alkaline earth metal chlorites; and a dry agent capable of reacting with said metal chlorite in the dry state to produce chlorine dioxide, said agent being selected from the group consisting of dry oxidizing agents, dry acids, and combinations thereof.

The instant invention thus provides a dry composition for the sustained, controlled release of chlorine dioxide. The compositions are characterized by being prepared using a completely dry process, thereby saving an energy intensive drying step. Further, the compositions of the invention are capable of producing chlorine dioxide while in a completely dry state without the need for water or water vapor. In addition, by varying the ratios of the components of the mixture, a wide range of chlorine dioxide release rates may be achieved. Also, the compositions are capable, upon agitation, or renewed generation of chlorine dioxide. The chlorine dioxide-releasing compositions of the invention may be used in the disinfection and deodorizing of enclosed spaces and in the preservation of boxed fruits and vegetables during shipment.

The nature and substance of the present invention, as well as its objects and advantages, will be more clearly perceived and fully understood by referring to the following description and claims.

DESCRIPTION OF THE PREFERRED EMBODIMENTS

The instant invention provides for the formulation of completely dry chlorine dioxide-releasing compositions that can continuously release chlorine dioxide without the addition of any other chemical, dry or wet, or the addition of water or water vapor in order to initiate and sustain the release of gaseous chlorine dioxide. The prior art discloses stabilized chlorine dioxide solutions or metal chlorite solutions that liberate chlorine dioxide on acidification as well as dry compositions that liberate chlorine dioxide upon addition of water. As stated previously herein, these prior art compositions have obvious drawbacks as well as the disadvantage of requiring action to be taken after manufacture in order to initiate and sustain the release of chlorine dioxide. The present invention, however, circumvents all of the foregoing disadvantages. In the compositions of this invention, the metal chlorite and the agent that reacts with the metal chlorite to release chlorine dioxide are separated or shielded by a dry, inert diluent. By regulating the particle size of the metal chlorite and the agent with which it reacts to generate chlorine dioxide, the available reactive surface area can be controlled. Similarly, by regulating the particle size and the amount of the diluent, the shielding surface area can be controlled. Thus the rate of production of gaseous chlorine dioxide can be determined and achieved by selection of the appropriate particle sizes and ratios of the inert and reactive materials. The greater the surface area of the reactants, the greater the rate of chlorine dioxide production.

Chlorine dioxide may be generated by reaction of a metal chlorite with an oxidizing agent such as chlorine or by reaction with an acidic material such as a mineral acid, an organic acid, or an acidic salt. The acid employed may be an oxidizing acid such as hypochlorous acid. The hypochlorous acid may conveniently be derived by acidifying a metal hypochlorite such as calcium hypochlorite or lithium hypochlorite. Examples of typical reactions by which chlorine dioxide may be generated from a metal chlorite are as follows:

$$2NaClO_2 + Cl_2 \rightarrow 2ClO_2 + 2NaCl \tag{1}$$

$$2NaClO_2 + HOCl \rightarrow 2ClO_2 + NaCl + NaOH \tag{2}$$

$$5NaClO_2 + 4HCl \rightarrow 4ClO_2 + 5NaCl + 2H_2O \tag{3}$$

Equation (1) shows the reaction of sodium chlorite with an oxidizing agent, i.e., chlorine, to generate chlorine dioxide. Equation (2) shows the generation of chlorine dioxide by the reaction of sodium chlorite with an oxidizing acid, i.e., hypochlorous acid. Equation (3) exemplifies the reaction of sodium chlorite with a mineral acid to generate chlorine dioxide. It will be understood by those skilled in the art that other oxidizing agents, oxidizing acids, and acids may also be used in the practice of this invention.

The dry compositions of this invention broadly comprise on a weight basis about 0.1%–95% of dry, inert diluent or shielding material; about 0.1%–80% of metal chlorite; and about 0.1%–75% of a dry agent capable of reacting with the metal chlorite in the dry state to produce chlorine dioxide. Preferably, the compositions of the invention comprise on a weight basis about 15%–50% of dry, inert diluent; about 5%–35% of metal chlorite; and about 1%–25% of a dry agent capable of reacting with the metal chlorite in the dry state to produce chlorine dioxide.

The metal chlorite is preferably an alkaline earth metal chlorite or an alkali metal chlorite. Examples of suitable metal chlorites are calcium chlorite, barium chlorite, magnesium chlorite, lithium chlorite, sodium chlorite, and potassium chlorite.

Examples of agents that are capable of reacting with a metal chlorite in the dry state to produce chlorine dioxide are oxidizing agents such as calcium hypochlorite and lithium hypochlorite. Examples of suitable acidic agents are citric acid, sodium bicarbonate, potassium dihydrogen phosphate, boric acid, oxalic acid, aluminum chloride, sodium fluosilicate, and sodium bisulfate. It will be understood by those skilled in the art that combinations of acidic agents and oxidizing agents may be used to react with the metal chlorite to generate chlorine dioxide.

Examples of dry, inert diluents include, but are not limited to, diatomaceous earth, sodium chloride, sodium silicate, disodium sulfate, and magnesium chloride as well as combinations thereof.

As mentioned above, the choice of particle size of the metal chlorite and the agent with which it reacts to generate chlorine dioxide may be varied to thereby vary the available reactive surface area. In this way, the rate of production of gaseous chlorine dioxide can be controlled.

Thus, the instant invention provides a dry composition for the sustained, controlled production of gaseous chlorine dioxide which is prepared from completely dry constituents and contains less than about 1% total moisture by weight, and preferably less than about 0.2% moisture by weight regardless of whether the water is present in the form of molecular water or hydrated components of the mixture. The prior art, such as that disclosed in U.S. Pat. No. 3,591,515, teaches a composition manufactured by adsorbing a sodium chlorite solution or a chlorine dioxide solution on an adsorbant to obtain a "substantially dry" chlorine dioxide-releasing composition with a moisture content that is much higher than that of the compositions of the present invention. The present invention involves no liquiid in the formulation of the composition and yields a truly dry chlorine dioxide-releasing composition.

This invention will be better understood by referring to the following specific examples, but it is not intended to be limited thereby.

EXAMPLE 1

A composition comprising 50.7% by weight of powdered diatomaceous earth (Celite grade 503), 18.42% by weight of granular adsorbant clay, 13.83% by weight of powdered sodium bicarbonate, 13.83% by weight of powdered technical grade sodium chlorite, and 3.22% by weight of granular citric acid were thoroughly mixed. The total moisture content of the composition was less than 0.2% by weight of water. Upon completion of mixing, 20 grams of the sample was placed in an enclosure and anhydrous argon gas was passed over the sample. The gas stream was subsequently scrubbed through a potassium iodide solution buffered at pH 7. Titration of the resultant iodine solution revealed that 0.05 mg. of chlorine dioxide was released over a one hour period. The sample was allowed to react for an additional 24 hours and retested in the same manner as above. Over a one hour period, 0.45 mg. of chlorine dioxide was released. The sample was then stored for one month and then retested as above. Chlorine dioxide in the amount of 0.15 mg. was released.

EXAMPLE 2

A composition comprising 50.7% by weight of powdered diatomaceous earth (Celite grade 503), 18.42% by weight of granular adsorbant clay, 13.83% by weight of powdered sodium bicarbonate, 13.83% by weight of powdered technical grade sodium chlorite,and 3.22% by weight of powdered citric acid were thoroughly mixed. The total moisture content of the composition was less than 0.2% by weight of water. Upon completion of mixing, 20 grams of the sample was placed in an enclosure, and anhydrous argon gas was passed over the sample. The gas stream was subsequently scrubbed through a potassium iodide solution buffered at pH 7. Titration of the resultant iodine solution revealed that 0.07 mg. of chlorine dioxide was released over a one hour period. The sample was allowed to react for 24 hours and retested in the same manner as above. Over a one hour period, 1.55 mg. of chlorine dioxide was released. The sample was then stored for one month and retested as above and found to release 0.22 mg. of chlorine dioxide over a one hour period. It can be seen that the powdered citric acid of this example with its greater surface area causes release of chlorine dioxide at a faster rate than does the granular citric acid of Example 1.

EXAMPLE 3

A composition comprising 37.5% by weight of powdered diatomaceous earth (Celite grade 503), 18.42% by weight of granular Iadsorbant clay, 13.83% by weight of powdered sodium bicarbonate, 21.2% by weight of powdered technical grade sodium chlorite, and 9.05% by weight of granular citric acid were thoroughly mixed. The total moisture content of the composition was less than 0.02% by weight of water. Upon completion of mixing, 20 grams of the sample was placed in an enclosure, and anhydrous argon gas was passed over the sample. The gas stream was subsequently scrubbed through a potassium iodide solution buffered at pH 7. Titration of the resultant iodine solution revealed that 0.01 mg. of chlorine dioxide was released over a one hour period. The sample was allowed to react for 24 hours and retested in the same manner as above. Over a one hour period, 1.25 mg. of chlorine dioxide was released. After being stored for one month and then retested as above, 0.55 mg. of hclorine dioxide was released in a one hour period.

EXAMPLE 4

A compositon comprising 51.0% by weight of powdered diatomaceous earth (Celite grade 503), 18.0% by weight of granular adsorbant clay, 14.0% by weight of powdered sodium bicarbonate, 13.83% by weight of powdered technical grade sodium chlorite, and 3.0% by weight of powdered calcium hypochlorite were thoroughly mixed. The total moisture content of the composition was less than 0.2% by weight of water. After being allowed to react for 24 hours, 20 grams of the sample was placed in an enclosure, and anhydrous argon gas was passed over the sample. The gas stream was subsequently scrubbed through a potassium iodide solution buffered at pH 7. Titration of the resultant iodine solution revealed that 7.70 mg. of chlorine dioxide was released over a one hour period.

EXAMPLE 5

A composition comprising 37% by weight of powdered diatomaceous earth (Celite grade 560), 24.0% by weight of granular sodium chloride, 10.0% by weight of powdered sodium carbonate, 28.0% by weigth of powdered technical grade sodium chlorite, and 1.0% by weight of granular oxalic acid were thoroughly mixed. The total moisture content of the composition was less than 0.2% by weight of water. After being allowed to react for 24 hours, 20 grams of the sample was placed in an enclosure, and anhydrous argon gas was passed over the sample. The gas stream was subsequently scrubbed through a potassium iodide solution buffered at pH 7. Titration of the resultant iodine solution revealed that 1.15 mg. of chlorine dioxide was released over a one hour period.

EXAMPLE 6

A composition comprising 5.0% by weight of powdered diatomaceous earth, 75.5% by weight of powdered sodium nitrate, 14.0% by weight of powdered technical grade sodium chlorite, and 5.5% by weight of powdered citric acid were thoroughly mixed. The total moisutre content of the composition was less than 0.02% by weight of water. After being allowed to react for 24 hours, 20 grams of the sample was placed in an enclosure, and anhydrous argon gas was passed over the sample. The gas stream was subsequently scrubbed through a potassium iodide solution buffered at pH 7. Titration of the resultant iodine solution revealed that 2.57 mg. of chlorine dioxide was released over a one hour period.

The compositions of this invention find utility in disinfecting and deodorizing enclosed spaces such as lockers and refrigerators. The foregoing is accomplished by placing in said enclosed space an effective amount of the composition for an appropriate period of time which is within the skill of the art to determine, to thereby accomplish said disinfecting and deodorizing. Similarly, boxed fruits and vegetables in shipment may be preserved by placing in the vicinity of said boxed fruits or vegetables an effective amount of a composition of this invention within a gas permeable container or pouch.

Thus, the instant invention provides dry compositions for the sustained, controlled release of gaseous chlorine dioxide. The compositions of this invention are characterized in that they are prepared in a completely anhydrous manner resulting in a composition having a very low moisture content without the need for an energy intensive drying step. Moreover, by the appropriate choice of particle sizes of the reactants and the diluent as well as their ratios, it is possible to vary the rate of chlorine dioxide release. The compositons of this invention find utility in disinfecting and deodorizing enclosed spaces as well as in the preservation of fruits and vegetables during shipment.

While specific embodiments of the present invention have been shown and described in detail to illustrate the utilization of the inventive principles, it is to be understood that such showing and description have been offered only by way of example and not by way of limitation. Protection by Letters Patent of this invention in all its aspects as the same are set forth in the appended claims is sought to the broadest extent that the prior art allows.

We claim as our invention:

1. A dry composition for the sustained, controlled production of gaseous chlorine dioxide comprising (1) a dry, inert diluent, (2) a dry metal chlorite selected from the group consisting of alkali metal chlorites and alkaline earth metal chlorites, and (3) a dry active agent capable of reacting with said dry metal chlorite in the dry state to produce chlorine dioxide, said active agent being selected from the group consisting of dry oxidizing agents, dry acids, and combinations thereof.

2. The dry composition of claim 1 wherein said dry composition comprises about 0.1% to about 95% by weight of said dry, inert diluent; about 0.1% to about 80% by weight of said dry metal chlorite; and about 0.1% to about 75% by weight of said dry agent which is capable of reacting in the dry state with said dry metal chlorite to produce chlorine dioxide.

3. The dry composition of claim 1 wherein said dry composition comprises about 15% to about 50% by weight of said dry, inert diluent; about 5% to about 35% by weight of said dry metal chlorite; and about 1% to about 25% by weight of said dry agent which is capable of reacting in the dry state with said dry metal chlorite to produce chlorine dioxide.

4. The composition of claim 1, wherein all the components of said composition are powders.

5. The composition of claim 1, wherein said diluent and said metal chlorite are powders and said agent which is capable of reacting in the dry state with said metal chlorite to produce chlorine dioxide is granular.

6. The composition of claim 1, wherein said diluent and said agent which is capable of reacting in the dry state with said metal chlorite to produce chlorine dioxide are powders and said metal chlorite is granular.

7. The composition of claim 1, wherein said agent which is capable of reacting in the dry state with said metal chlorite to produce chlorine dioxide is a combination of a dry oxidizing agent and a dry acid.

8. The composition of claim 1, wherein said metal chlorite is selcted from the group consisting of calcium chlorite and sodium chlorite; said agent which is capable of reacting in the dry state with said metal chlorite to produce chlorine dioxide is selected from the group consisting of calcium hypochlorite, lithium hypochlorite, citric acid, oxalic acid, sodium bicarbonate, potassium dihydrogen phosphate, sodium bisulfate, and combinations thereof; and said dry, inert diluent is selected from the group consisting of diatomaceous earth, adsorbant clay, sodium chloride, sodium nitrate, disodium carbonate, and mixtures thereof.

9. A dry composition for the sustained, controlled production of gaseous chlorine dioxide comprising:
approximately 51% by weight of dry diatomaceous earth, approximately 18% by weight of dry absorbent clay, approximately 14% by weight of dry sodium bicarbonate, approximately 14% by weight of dry technical grade sodium chlorite and approximately 3% by weight of dry citric acid.

10. A dry composition for the sustained, controlled production of gaseous chorine dioxide comprising:
approximately 38% by weight of dry diamostaceous earth, approximately 14% by weight of dry absorbent clay, 18% by weight of dry sodium bicarbonate, approximately 21% by weight of dry technical grade sodium chlorite and approximately 9% by weight of dry citric acid.

11. A dry composition for the sustained controlled, production of gaseous chlorine dioxide comprising:
approximately 51% by weight of dry diatomaceous earth, approximately 18% by weight of dry absorbent clay, approximately 14% by weight of dry sodium bicarbonate, approximately 14% by weight of dry technical grade sodium chlorite and approximately 3% by weight of dry calcium hypochlorite.

12. A dry composition for the sustained controlled production of gaseous chlorine dioxide comprising:
approximately 37% by weight of dry diatomaceous earth, approximately 24% by weight of dry sodium chloride, approximately 10% by weight of dry sodium carbonate, approximately 28% by weight of dry technical grade sodium chlorite, and approximately 1% by weight of dry oxalic acid.

13. A dry composition for the sustained, controlled production of gaseous chlorine dioxide comprising:
approximately 5% by weight of dry diatomaceous earth; approximately 75.5% by weight of dry sodium nitrate, approximately 14% by weight of dry technical grade sodium chlorite and approximately 5.5% by weight of dry citric acid.

* * * * *